US006932776B2

(12) United States Patent
Carr

(10) Patent No.: US 6,932,776 B2
(45) Date of Patent: Aug. 23, 2005

(54) METHOD AND APPARATUS FOR DETECTING AND TREATING VULNERABLE PLAQUES

(75) Inventor: Kenneth L. Carr, Woolwich, ME (US)

(73) Assignee: Meridian MedicalSSystems, LLC, Ayer, MA (US)

(*) Notice: Subject to any disclaimer, the term of this patent is extended or adjusted under 35 U.S.C. 154(b) by 0 days.

(21) Appl. No.: 10/452,154

(22) Filed: Jun. 2, 2003

(65) Prior Publication Data

US 2004/0243004 A1 Dec. 2, 2004

(51) Int. Cl.[7] ................................................. A61B 5/00
(52) U.S. Cl. ..................................... 600/549; 374/122
(58) Field of Search ............................... 600/430, 549; 607/100–102, 122

(56) References Cited

U.S. PATENT DOCUMENTS

| 4,557,272 | A | 12/1985 | Carr |
| 4,583,556 | A | 4/1986 | Hines et al. |
| 5,057,106 | A | 10/1991 | Kasevich et al. |
| 5,904,709 | A | 5/1999 | Arndt et al. |
| 6,047,216 | A | 4/2000 | Carl et al. |
| 6,210,367 | B1 | 4/2001 | Carr |
| 6,408,204 | B1 | 6/2002 | Hirschman |
| 6,475,159 | B1 | 11/2002 | Casscells et al. |
| 6,496,736 | B1 | 12/2002 | Carl et al. |
| 6,496,738 | B2 | 12/2002 | Carr |
| 6,860,851 | B2 * | 3/2005 | Knudson et al. ............ 600/309 |
| 2002/0103445 | A1 | 8/2002 | Rahdert et al. |
| 2002/0111560 | A1 | 8/2002 | Kokate et al. |

OTHER PUBLICATIONS

Diller, Wendy "The Coming of Age of Vulnerable Plaque", Windhover Information Inc. Start–up Nov. 2000, pp. 1–10.

* cited by examiner

Primary Examiner—Francis J. Jaworski
(74) Attorney, Agent, or Firm—Cesari and McKenna, LLP; John F. McKenna

(57) ABSTRACT

Apparatus for detecting vulnerable plaques embedded in the wall of a patient's blood vessel includes an intravascular catheter containing a microwave antenna, an extra-corporeal radiometer having a signal input, a reference input and an output, a cable for electrically connecting the antenna to the signal input, and a device for applying an indication of the patient's normal tissue temperature to the reference input so that when the catheter is moved along the vessel, the locations of the vulnerable plaques are reflected in a signal from the output as thermal anomalies due to the higher emissivity of the vulnerable plaques as compared to the normal tissue. A second embodiment of the apparatus has two coaxial antennas in the catheter serving two radiometers. One measures the temperature at locations in the vessel wall, the other measures the temperature at the surface. By subtracting the two signals, the locations of vulnerable plaque may be visualized. The apparatus employs a special diplexer for separating the signals from the two antennas and a method of detecting and possibly destroying the plaques is also disclosed.

18 Claims, 3 Drawing Sheets

METHOD AND APPARATUS FOR DETECTING AND TREATING VULNERABLE PLAQUES

This invention relates to a minimally invasive technique for detecting vulnerable plaques. It relates especially to method and apparatus for detecting vulnerable plaques utilizing microwave radiometry.

BACKGROUND OF THE INVENTION

1. Field of the Invention

It is widely known that many heart attacks originate from blockages created by athrosclerosis which is the aggressive accumulation of plaques in the coronary arteries. The accumulation of lipids in the artery and resulting tissue reaction cause a narrowing of the affected artery which can result in angina, coronary occlusion and even cardiac death.

Relatively recent studies have shown that coronary disease can also be caused by so-called vulnerable plaques which, unlike occlusive plaque, are engrained or imbedded in the arterial wall and do not grow into the blood vessel. Rather, they tend to erode creating a raw tissue surface that forms caps or scabs. Thus, they are more dangerous than occluding plaque which usually give a warning to a patient in the form of pain or shortness of breath. See, e.g., The Coming of Age of Vulnerable Plaque, Diller, W., Windover's Review of Emerging Medical Ventures, November 2000.

2. Description of the Prior Art

Since vulnerable plaques are contained within the vessel wall, they do not result in a closing or narrowing of that vessel. As a result, such plaques are not easily detectable using conventional x-ray, ultrasound and MRI imaging techniques.

Moreover, since vulnerable plaques are part of the vessel wall, they may have essentially the same temperature as the surrounding normal tissue and the blood flowing through the vessel. Therefore, they are not amenable to detection by known intravascular catheters which rely on infrared (IR) imaging, thermisters, thermocouples and the like in order to detect temperature differences in the vessel wall.

Such intravascular catheters are disadvantaged also because they usually incorporate an inflatable balloon to isolate the working each end of the catheter from fluids in the vessel; see for example U.S. Pat. No. 6,475,159. As seen there, the IR detector is located within the balloon which constitutes an insulating (not transparent at IR frequencies) layer between the detector and the vessel wall causing significant attenuation of the signal from the detector. Also, the undesirable stoppage of blood flow by the balloon increases the risk to the patient. Still further, the balloon has to be repeatedly inflated and deflated in order to image different locations along the blood vessel increasing the operating time during which the patient is at risk.

SUMMARY OF THE INVENTION

Accordingly, it is an object of the present invention to provide a method of detecting vulnerable plaques before the plaques rupture and cause thrombosis.

Another object of the invention is to provide such a vulnerable plaque detection method which does not require the stoppage of blood flow in the affected vessel.

An additional object of the invention is to provide a method of detecting vulnerable plaques using microwave radiometry.

Another object of the invention is to provide intracorporeal microwave apparatus for detecting vulnerable plaques having one or more of the above advantages.

A further object of the invention is to provide such apparatus capable of treating the plaques after detection.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in the following detailed description, and the scope of the invention will be indicated in the claims.

Briefly, the present method utilizes microwave radiometry to detect the presence of vulnerable plaques engrained in the wall of a blood vessel. In accordance with the method, an intravascular catheter containing at least one microwave antenna is moved along the suspect vessel. The antenna, in combination with an external microwave detection and display unit, is able to detect and display thermal anomalies due to the difference in the thermal emissivity (brightness) of vulnerable plaques as compared to normal tissue even though the two may have a common temperature. In other words, it has been found that the microwave characteristics of vulnerable plaques imbedded in a vessel wall are different from those of normal tissue comprising the vessel wall and this difference is detected as a thermal anomaly and displayed or plotted as the catheter is moved along the vessel.

As we shall see, in some applications the detected plaques may then by treated by microwave ablation using the very same catheter.

In its simplest form, the microwave antenna may be a more or less conventional microwave antenna located at the distal or working end of the catheter. The inner and outer conductors of the antenna are connected by a coaxial cable to an external detection and display unit which detects the microwave emissions from the blood vessel picked up by the antenna and produces corresponding output signals for a display which responds to those signals by displaying the thermal emissions from the blood vessel in real time as the catheter is moved along the vessel.

In accordance with the invention, the radiometer is preferably a Dicke switch-type radiometer and the temperature of the blood flowing through the vessel, which corresponds to the body's core temperature, is used as the radiometer reference. The operating frequency of the radiometer is selected to detect microwave emissions from a depth in the blood vessel wall where vulnerable plaques are likely to be imbedded, e.g. a frequency in the range of 1 to 4 GHz, preferably 1 GHz. Thus as the catheter is moved along the vessel, it is maintained at a constant background or core temperature corresponding to the temperature of the blood and of normal tissue. The locations of vulnerable plaques are detected as thermal anomalies (hot spots) due to the higher emissivity of the plaques as compared to normal tissue. Using the output of the radiometer to control a display, the plaque sites along the vessel can be plotted.

It is important to note that the present method and apparatus allow the detection of vulnerable plaques at subsurface locations in the vessel wall without contacting the vessel wall and without any interruption of blood flow through the vessel.

As will be described in more detail later, the catheter may include a lengthwise passage for receiving a guide wire to help guide the catheter into and along the blood vessel being examined. As we shall see, in some applications the guide wire itself may actually constitute the inner conductor of the antenna within the catheter. Also, in order to help center the antenna within the blood vessel, the catheter may incorporate an expandable perforated standoff device which spaces the antenna from the vessel wall without materially interfering with the blood flow through the vessel.

In a preferred embodiment of the invention, the detection unit includes two radiometers operating at different frequencies. One radiometer, operating at a higher frequency in the range of 3 to 6 GHz, preferably 4 GHz, detects thermal emissions from the inner surface of the blood vessel. This temperature, corresponding to the body core temperature, is used as a reference. The second radiometer operates at a lower frequency of 1 to 4 GHz, preferably 1 GHz, to detect thermal emissions from subsurface locations in the vessel wall which may contain embedded vulnerable plaques. Thus by subtracting the outputs of the two radiometers, the sites of vulnerable plaques can be detected and displayed continuously and in real time as the catheter is moved along the blood vessel.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF ILLUSTRATIVE EMBODIMENTS

Figure 1:
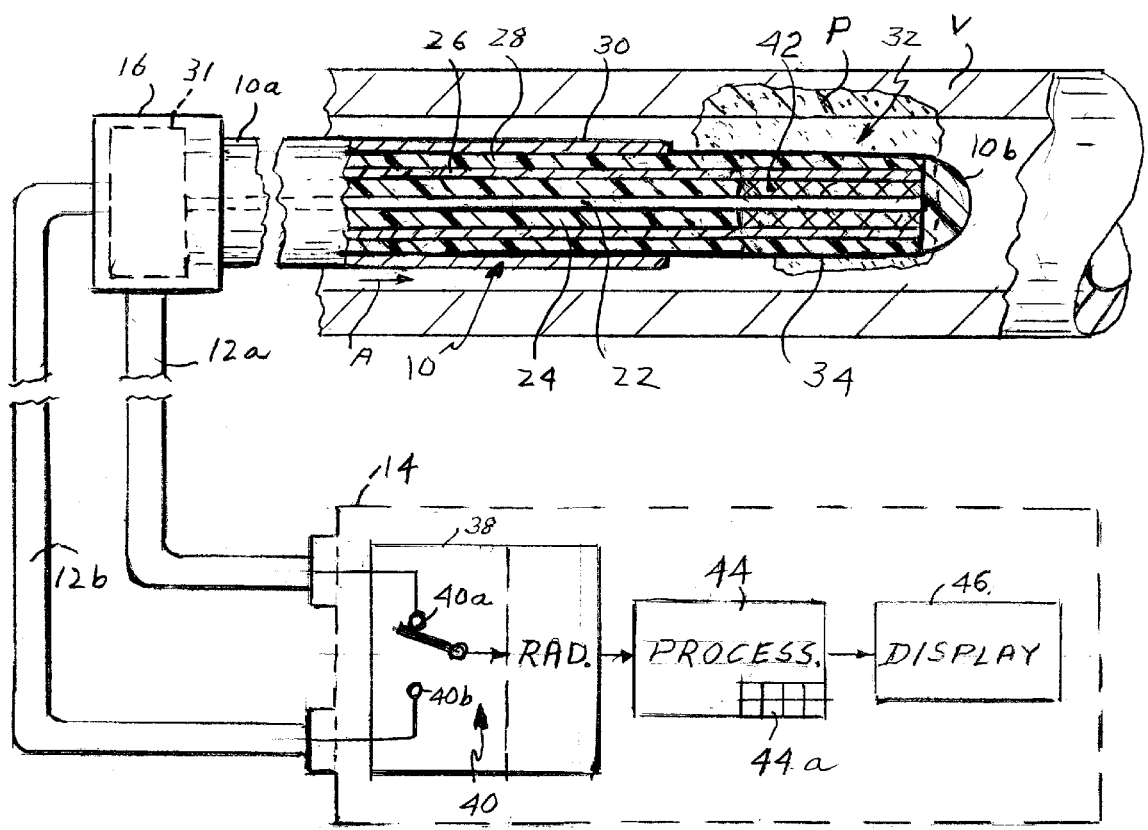
FIG. 1 is a diagrammatic view of apparatus for detecting vulnerable plaques in accordance with the invention and employing a first intravascular catheter embodiment.

Referring to FIG. 1 of the drawings, the present apparatus comprises a catheter shown generally at 10 for insertion into a blood vessel V which may have locations where vulnerable plaques P are embedded or engrained in the vessel wall. Such plaques P typically include a relatively large portion of the vessel wall, e.g. a third to a half of its circumference. Catheter 10 is connected by coaxial cables 12a and 12b to a detection and display unit 14. The catheter has a proximal end 10a to which cables 12a and 12b are connected by way of a fitting or connector 16 and a distal end or tip 10b. The catheter may have a length of 100 cm or more and is quite narrow and flexible so that it can be threaded along a conventional introducer, e.g. 8.5 French, allowing the distal end 10b of the catheter to be placed at a selected position in a patient's blood vessel V. Typically, vessel V is accessed by a vein in the patient's neck or groin.

The catheter may include an expandable perforated standoff device such as shown U.S. Pat. No. 6,496,738, which is hereby incorporated herein by reference, so as to center the catheter 10 in vessel V without impeding the blood flow through that vessel.

Figure 5:
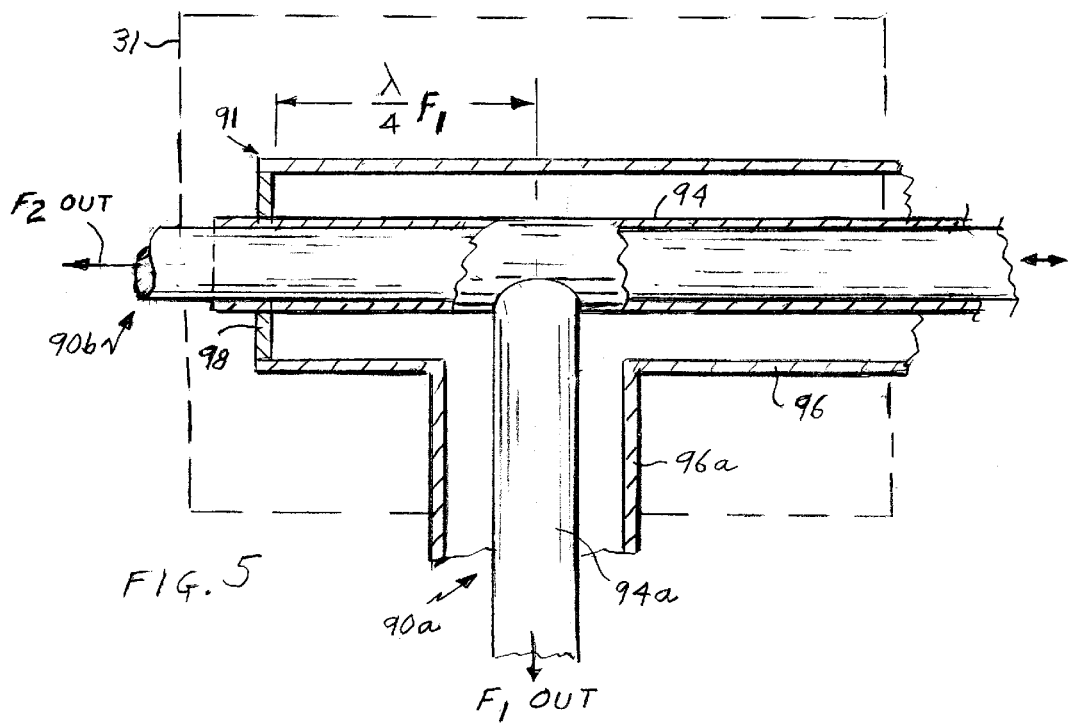
FIG. 5 is a sectional view of the diplexer component of the apparatus.

As shown in FIG. 1, catheter 10 comprises a central conductor 22 surrounded by a cylindrical layer 24 of a suitable low loss dielectric material. Surrounding the layer 24 is a tubular middle conductor 26 surrounded by a dielectric layer 28. Finally, a tubular outer conductor 30 encircles layer 28. At fitting 16, the proximal ends of conductors 22, 26 and 30 are connected by way of a passive diplexer 31 (FIG. 5) to the coaxial cables 12a and 12b. Preferably, the catheter has a protective outer coating, e.g. of PTFE, (not shown).

At the distal end segment of catheter 10, the middle conductor 26 extends beyond the outer conductor 30 to form a microwave antenna 32 which, in this case, is a monopole as in the above U.S. Pat. No. 6,496,738. In some applications, a helical antenna or capacitive tip may be used; see U.S. Pat. Nos. 4,583,556 and 4,557,272, the contents of which are hereby incorporated herein by reference.

The distal end 10b of the catheter is actually formed by a rounded low loss dielectric button 34 which is butted and secured to the distal end of the dielectric layers 24 and 28. Typically, the middle conductor 26 extends beyond the outer conductor 30 a distance in the order of 1 cm so that antenna 32 has a relatively long antenna pattern. Also, if desired, the diameters of the coaxial conductors in catheter 10 may be stepped down along the catheter to improve antenna performance. Antenna 32 detects the thermal radiation emitted from blood vessel V and applies a corresponding electrical signal via cable 12a to a radiometer 38 in unit 14. The radiometer 38 may be a conventional Dicke switch-type radiometer as described in the above U.S. Pat. No. 4,557,272. The temperature-indicating signal from antenna 32 is applied via cable 12a to the signal input 40a of the Dicke switch 40 in radiometer 38. The other input to the switch 40 is a reference value which corresponds to the patient's core temperature, e.g. 37° C.

That temperature may be measured using a resistive termination or load or heat sensor 42 connected between inner conductor 22 and middle conductor 26 near the catheter tip. The sensor output or value is applied via those conductors to diplexer 31 in connector 16 which separates that signal from the antenna signal. That reference signal is thereupon conducted by cable 12b to the reference input 40b of switch 40. In other words, two ports of the radiometer are brought out to receive both the antenna and reference signals from catheter 10. The advantage of this arrangement is that the unknown temperature is now compared with the actual blood (core) temperature. This improves radiometer sensitivity (performance) by keeping all circuitry that precedes the Dicke switch at the same temperature.

The radiometer operates at a center frequency in the order of 1 to 4 GHz so that the apparatus can detect thermal emissions from locations relatively deep in the wall of vessel V.

The output of the radiometer 38 is processed by a processor 44 in unit 14 which controls a display 46.

To use the FIG. 1 apparatus, the catheter 10 is threaded into the patient's vessel V in the usual way. After insertion, the catheter assumes essentially the same temperature as the vessel V and the blood flowing through the vessel. This temperature as sensed by sensor 42 is used as the reference for Dicke switch 40 which toggles between its signal and reference inputs 40a and 40b in the usual way. When the catheter is moved along the vessel V, say, in the direction of the arrow A, the antenna 32 will pick up thermal emissions from the normal tissue in the vessel wall and unit 14 will provide a core or background temperature indication which will be displayed by display 46. However, when the antenna 34 is moved opposite a region containing vulnerable plaques P, the apparatus will detect a thermal anomaly due to the increased emittance (brightness) of the plaques embedded in the vessel wall. Thus as the catheter 10 is moved along the vessel, the unit 14 can display continuously in real time the locations of plaques P as well as other useful information such as the body's core temperature, diagnostic data and the like as instructed via the processor's keyboard 44a.

Figure 2:
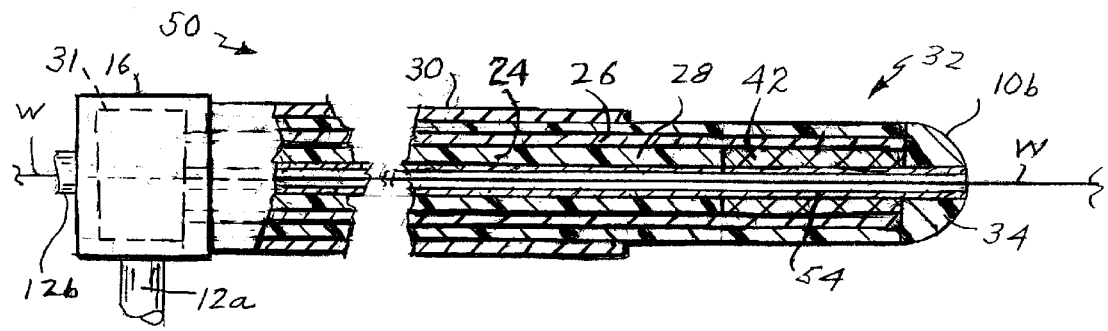
FIG. 2 is a fragmentary sectional view of a second catheter embodiment for use with the FIG. 1 apparatus.

Referring now to FIG. 2, in some procedures, it may be desirable that the catheter be guided along the blood vessel V by means of a guide wire. FIG. 2 illustrates an intravascular catheter shown generally at 50 capable of being moved along a guide wire W previously introduced into the blood vessel in a conventional manner. Catheter 50 is similar to catheter 10 in FIG. 1 except that its central conductor 54 is an elongated flexible conductive tube. The other parts of catheter 50 are more or less the same as those of catheter 10 and therefore carry the same identifying numerals.

In catheter 50, conductor 54 extends through the fitting 16 as well as all the way through the button 34 to the tip 10b of the catheter. This allows the guide wire W to be threaded through the tubular conductor 54 so that the catheter 50 can be moved along the guide wire after the guide wire has been introduced into the blood vessel being examined.

When the catheter 50 is in use, the guide wire W does not interfere with the antenna pattern of antenna 32 because it is shielded by conductor 54. In other words, the field around the antenna does not extend within the metal conductor 54.

Figure 3:
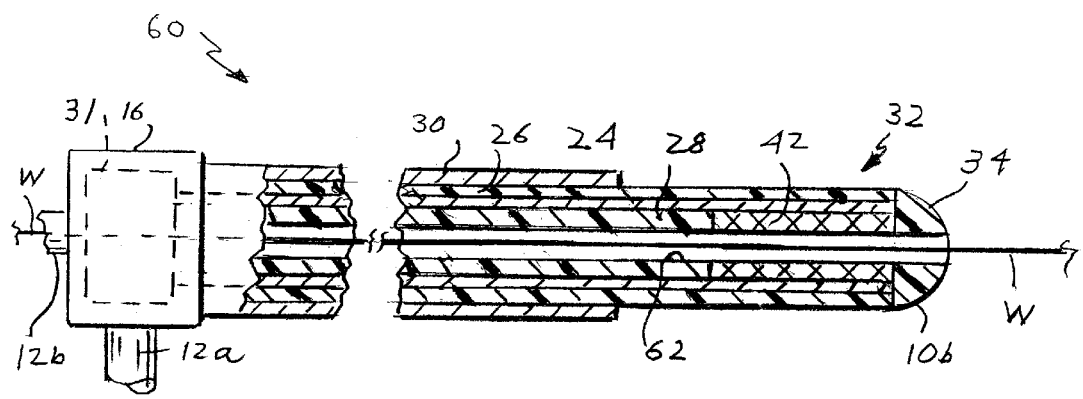
FIG. 3 is a similar view showing a third catheter embodiment.

In some applications, the guide wire W itself may be used as the central conductor of the antenna 32 in the catheter. FIG. 3 shows such a catheter at 60 which may be used to detect vulnerable plaques as described above. As shown there, the catheter 60 is similar to catheter 50 except that it is devoid of the tubular central conductor 54. Instead, it is formed with an axial passage 62 in dielectric layer 24 and button 34 which passage extends snugly but slidably all the way from the tip of the catheter to the proximal end thereof and through the fitting 16 so that the guide wire W can be threaded through passage 62 as shown. In this case, the guide wire itself is connected electrically via cable 12b to the detection and display unit 14. In use, the guide wire may be introduced into the blood vessel to be examined and then remain stationary while the remainder of the catheter is slid along the guide wire in order to examine different lengthwise segments of the blood vessel wall. Alternatively, the entire catheter 60 including the guide wire W may be moved as a unit along the blood vessel in order to advance the antenna 32 along that vessel.

Figure 4:
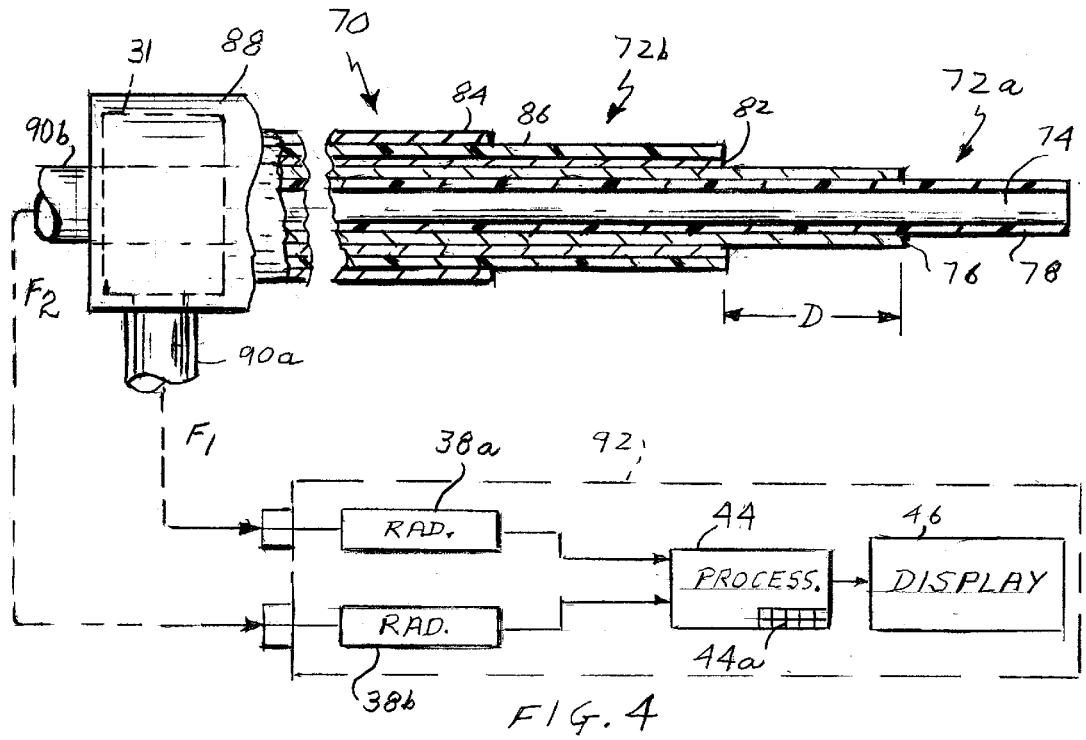
FIG. 4 is a view similar to FIG. 1 of another apparatus embodiment.

Refer now to FIG. 4 which shows a preferred embodiment of the invention that can detect even very small thermal anomalies in the vessel wall due to embedded or engrained plaques. The FIG. 4 apparatus comprises a catheter shown generally at 70 having coaxial inner and outer antennas indicated at 72a and 72b. The inner antenna 72a comprises an inner conductor 74 and an outer conductor 76 separated by an insulating layer 78. The inner conductor 74 extends beyond the outer conductor 76 forming the antenna 72a.

The outer antenna 72b comprises a tubular inner conductor 82 and an outer conductor 84 separated by an insulating layer 86, the inner conductor 72 being insulated from conductor 76 and extending beyond the outer conductor 74 to form the outer antenna 72b. The proximate end of catheter 70 is terminated by a fitting or connector 88 containing a diplexer 31 (FIG. 5) which connects the conductors of the antennas 72a,72b to coaxial cables 90a and 90b leading to a detection and display unit 92.

In some applications, the outer conductor 76 of antenna 72a and the inner conductor 82 of antenna 72b may be fixed relatively. More preferably, those conductors are separate as shown so that the inner antenna 72a is slidable within the outer antenna 72b and fitting 88 so that the distance D between the two antennas can be varied from zero to several centimeters allowing the outer and inner antennas to be optimized at two specific frequencies $F_1$ and $F_2$. The inner conductor 74 of antenna 72a may be hollow or tubular so that it can receive a guide wire as described in connection with FIG. 2. Alternatively, that conductor may be sufficiently small to serve as the guide wire itself as described in connection with FIG. 3.

In order to electrically separate the outputs of the two antennas 72a and 72b, the fitting or connector 88, like connector 16, incorporates a passive diplexer 31. As seen from FIG. 5, the diplexer includes a quarter-wave ($\lambda/4$) stub 91 to bring out the signal $F_2$ from the inner antenna 72a. This stub also provides a matched 90° bend to separate and bring out the signal $F_1$ from the outer antenna 72b.

Whereas it is known in the art to use a quarter-wave stub to support the center conductor of an antenna, the present diplexer has a tubular inner conductor 94 which receives the coaxial cable 74–78 comprising the inner antenna 72a providing signal $F_2$. That conductor 94 may be an extension of the antenna conductor 82. Surrounding and insulated from conductor 94 is a coaxial outer conductor 96 which may be an extension of antenna conductor 84. The two diplexer conductors 94 and 96 are shorted by an end plate 98 at the end of stub 91. Conductor 94 has a branch 94a which is brought out through a branch 96a of conductor 96 to deliver the signal $F_1$ from antenna 72b. Preferably, the coaxial cable 74–78 is slidable to some extent along conductor 94 to vary the antenna distance D as described above.

The illustrated diplexer 31 provides several distinct advantages. It separates the concentric cables from antennas 72a and 72b in FIG. 4 into two separate cables; allows those cables to be mechanically and independently positioned, and it allows the innermost conductor to double as a guide wire for the catheter as shown in FIGS. 2 and 3.

In the FIG. 4 apparatus, the smaller diameter antenna 72a, optimized at a frequency $F_2$, e.g. 3–6 GHz, may measure the blood and normal tissue temperature, whereas the larger diameter antenna 72b optimized at frequency $F_2$, e.g. 1–4 GHz, measures the temperature of the deeper tissue where vulnerable plaques are likely to occur. This larger diameter provides a less lossy cable making that antenna more efficient. The larger diameter antenna also places it closer to the wall of vessel V (FIG. 1), further increasing the depth of detection.

While the catheter 70 in FIG. 4 could be connected by cables 90a and 90b to the switch 40 of a single radiometer as shown in FIG. 1, the illustrated detection and display unit 92 contains two radiometers 38a and 38b connects to cables 90a and 90b, respectively. The former which operates at the frequency $F_1$ detects thermal anomalies picked up by antenna 72b due to plaques located relatively deep in the wall of vessel V (FIG. 1) as before; the latter operating at frequency $F_2$ detects thermal emissions picked up by antenna 72a at the inner surface of the vessel which reflect the body core temperature. The processor 44 thereupon subtracts the signals and causes display 46 to display the locations of thermal anomalies which are likely due to plaques P.

After the vessel V has been examined and the locations of the plaques P determined as described above, the plaques P may be treated by microwave ablation using the very same catheter. This may be done by connecting the catheter via a diplexer to a microwave transmitter in order to heat the plaques as described in the above U.S. Pat. No. 6,496,738.

It will thus be seen that the objects set forth above, among those made apparent from the preceding description, are efficiently attained and, since certain changes may be made in carrying out the above method and in the constructions set forth without departing from the scope of the invention, it is intended that all matter contained in the above description or shown in the accompanying drawings shall be interpreted as illustrative and not in the limiting sense.

Is also to be understood that the following claims are intended to cover all of the generic and specific features of the invention described herein.

What is claimed is:

1. Apparatus for detecting vulnerable plaques embedded or engrained in the wall of a patient's blood vessel, said apparatus comprising
an intravascular catheter containing a microwave antenna;
a radiometer having a signal input, a reference input and an output;
a diplexer electrically connecting the antenna to the signal input, and
means for applying an indication of the patient's normal tissue temperature to the diplexer which routes said indication to the reference input so that when the catheter is moved along said vessel, the locations of said vulnerable plaques are reflected in a signal from said output as thermal anomalies due to the higher emissivity of said vulnerable plaques as compared to normal tissue.

2. The apparatus defined in claim 1 wherein the antenna comprises a coaxial cable extending lengthwise along the catheter.

3. The apparatus defined in claim 2 wherein the coaxial cable is stepped along its length to optimize its performance.

4. The apparatus defined in claim 2 wherein the coaxial cable has an outer conductor and an inner conductor electrically insulated from the outer conductor and which extends lengthwise beyond the outer conductor.

5. The apparatus defined in claim 4 wherein the inner conductor is an open-ended tube which extends the length of the catheter and is adapted to receive a guide wire.

6. The apparatus defined in claim 5 and further including a guide wire slidably received in said tube for guiding the catheter along said blood vessel.

7. The apparatus defined in claim 4 wherein the inner conductor consists of a conductive wire slidably received within and insulated from the outer conductor, said wire constituting both the inner conductor of said antenna and a guide wire for the catheter.

8. The apparatus defined in claim 1 wherein said radiometer has an operating frequency in the range of 1 to 4 GHz.

9. The apparatus defined in claim 1 and further including display means responsive to the output signal from the radiometer for displaying the locations of said thermal anomalies along said blood vessel.

10. The apparatus defined in claim 1 wherein said means for applying comprise
temperature sensing means in the catheter, and
a cable connecting the output of the sensing means to said diplexer.

11. The apparatus defined in claim 10 wherein said temperature sensing means include an impedance in said catheter.

12. Apparatus for detecting vulnerable plaques embedded or ingrained in the wall of a patient's blood vessel, said apparatus comprising
an intravascular catheter containing a microwave antenna and a temperature sensor;
a radiometer having a signal input, a reference input and an output and operating at a selected frequency;
a diplexer connecting the antenna and sensor to the signal and reference inputs, respectively, of said radiometer so that when the catheter is moved along said blood vessel, said radiometer output delivers a plaque-indicating output signal, and
means responsive to the output signal for displaying thermal anomalies due to the higher emissivity of said vulnerable plaques as compared to normal tissue.

13. The apparatus defined in claim 12 wherein the antenna comprises a coaxial cable composed of electrically isolated inner and outer conductors extending lengthwise within the catheter, said inner conductor extending beyond the outer conductor.

14. The apparatus defined in claim 13 wherein the inner conductor is an open-ended tube.

15. The apparatus defined in claim 14 and further including a guide wire slidably received in said tube for guiding the catheter along said blood vessel.

16. The apparatus defined in claim 12 wherein the inner conductor consists of a conductive wire slidably received within the outer conductor, said wire also constituting a guide wire for the catheter.

17. The apparatus defined in any one of claims 1 or 12, wherein said catheter also includes
a radially expandable perforate stand-off device, and
means operable extracorporeally for expanding said device.

18. The apparatus defined in any one of claims 1 or 12, and further including
a microwave transmitter for transmitting a heating signal capable of ablating tissue, and
means including an additional diplexer for coupling the heating signal to the antenna but not to the radiometer (s) so that the apparatus can heat said vulnerable plaques after the detection thereof.

* * * * *